US012630695B2

(12) United States Patent
Kawaji et al.

(10) Patent No.: US 12,630,695 B2
(45) Date of Patent: May 19, 2026

(54) RESIN COMPOSITION COMPRISING TWO TYPES OF PARTICLES FOR ACOUSTIC MEMBER, ULTRASOUND TRANSDUCER, ULTRASOUND PROBE, AND ULTRASOUND DIAGNOSTIC APPARATUS

(71) Applicant: Konica Minolta, Inc., Tokyo (JP)

(72) Inventors: Munenori Kawaji, Tokyo (JP); Yoshikazu Ojima, Tokyo (JP); Kiyokazu Morita, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 254 days.

(21) Appl. No.: 17/828,633

(22) Filed: May 31, 2022

(65) Prior Publication Data

US 2022/0389192 A1 Dec. 8, 2022

(30) Foreign Application Priority Data

Jun. 7, 2021 (JP) ................................. 2021-095163

(51) Int. Cl.
*C08K 7/00* (2006.01)
*A61B 8/00* (2006.01)
(Continued)

(52) U.S. Cl.
CPC .............. *C08K 7/00* (2013.01); *A61B 8/4444* (2013.01); *C08K 3/22* (2013.01); *C08K 5/5419* (2013.01);
(Continued)

(58) Field of Classification Search
CPC ........ C08K 13/00; C08K 13/02; C08K 13/04; C08K 2003/2272; C08K 2003/2275; C08K 5/00; C08K 5/54
See application file for complete search history.

(56) References Cited

U.S. PATENT DOCUMENTS

| | | | | |
|---|---|---|---|---|
| 2005/0127793 A1* | 6/2005 | Baumgartner | ....... | G10K 11/002 310/334 |
| 2007/0282204 A1* | 12/2007 | Yamashita | ............. | G10K 11/02 600/459 |
| 2016/0338666 A1* | 11/2016 | Morita | ................. | A61B 8/4444 |
| 2017/0009072 A1* | 1/2017 | Kobayashi | ......... | C08G 59/4085 |

FOREIGN PATENT DOCUMENTS

| | | |
|---|---|---|
| JP | H03-172096 A | 7/1991 |
| JP | H11252695 A | 9/1999 |

(Continued)

OTHER PUBLICATIONS

Translation JP 2016192666 A (Year: 2016).*
Notice of Reasons for Refusal dated Nov. 26, 2024, issued for the corresponding Japanese patent application No. 2021-095163, 9 pages, with English translation.
(Continued)

*Primary Examiner* — Hoa (Holly) Le
(74) *Attorney, Agent, or Firm* — LUCAS & MERCANTI, LLP

(57) ABSTRACT

The present invention provides a resin composition used for producing an acoustic member, the resin composition comprising: a thermosetting resin; and two or more types of particles dispersed in the thermosetting resin, the two or more types of particles comprising: heavy particles that have a higher density than the thermosetting resin and are particles other than metal particles; and light particles that have a lower density than the thermosetting resin, and the total content of the heavy particles and the light particles relative to the entire volume of a cured product of the resin composition being 10 vol % or more.

11 Claims, 2 Drawing Sheets

(51) Int. Cl.
   *C08K 3/22* (2006.01)
   *C08K 5/5419* (2006.01)

(52) U.S. Cl.
   CPC ................ *C08K 2003/2258* (2013.01); *C08K 2003/2272* (2013.01); *C08K 2201/005* (2013.01); *C08K 2201/014* (2013.01)

(56) References Cited

FOREIGN PATENT DOCUMENTS

| | | | |
|---|---|---|---|
| JP | 2000-115893 | A | 4/2000 |
| JP | 2005-177479 | A | 7/2005 |
| JP | 2012-235524 | A | 11/2012 |
| JP | 2014168489 | A | 9/2014 |
| JP | 2016192666 | A | 11/2016 |

OTHER PUBLICATIONS

Notice of Reasons for Refusal, dated Jun. 10, 2025, which was issued for the corresponding Japanese Patent Application No. 2021-095163, 11 pages, with English translation.
Office Action, dated Nov. 4, 2025, which was issued for the corresponding Japanese Patent Application No. 2021-095163, 8 pages, with English translation.

\* cited by examiner

1

RESIN COMPOSITION COMPRISING TWO TYPES OF PARTICLES FOR ACOUSTIC MEMBER, ULTRASOUND TRANSDUCER, ULTRASOUND PROBE, AND ULTRASOUND DIAGNOSTIC APPARATUS

CROSS REFERENCE TO RELATED APPLICATIONS

The entire disclosure of Japanese Patent Application No. 2021-095163 filed on Jun. 7, 2021, is incorporated herein by reference in its entirety.

BACKGROUND

Technological Field

The present invention relates to a resin composition, an acoustic member, an ultrasound transducer, an ultrasound probe, and an ultrasound diagnostic apparatus.

Description of Related Art

Ultrasound probes are connected to or configured to be able to communicate with ultrasound diagnostic apparatuses, and are used to obtain the shape and movement of biological tissues as diagnostic images through a simple operation of placing them on the surface of the body or inserting them inside the body.

The ultrasound probe has a piezoelectric material, which transmits and receives ultrasound, and an acoustic lens, which is placed in close contact with the living body. An acoustic matching layer is disposed between them, and a backing material is disposed on the piezoelectric material on the side opposite to the living body. The acoustic matching layer is a member for changing the ultrasound from the piezoelectric material to the acoustic lens so as to reduce the difference in acoustic impedance. The acoustic matching layer prevents the ultrasound from being reflected between the piezoelectric material and the living body, which can improve the accuracy of diagnostic images. The backing material is a member that attenuates the ultrasound transmitted from the piezoelectric material to the opposite side of the living body. As such an acoustic matching layer and a backing material, a variety of materials are known.

For example, Japanese Patent Application Laid-Open No. 2000-115893 discloses an acoustic matching layer formed by providing a pair of limiting materials with a constant height dimension on a piezoelectric plate, applying a molten resin of the same material as the above-described limiting materials, and pressing the above-described molten resin from the top surface. According to Japanese Patent Application Laid-Open No. 2000-115893, it is said that, by providing the limiting materials and pressing the molten resin of the same material as them, the acoustic matching layer has a uniform thickness and a small variation, is highly economical, and provides good transmitting and receiving characteristics of the ultrasound probe.

Also, Japanese Patent Application Laid-Open No. 03-172096 discloses an acoustic matching layer in which, to a piezoelectric transducer, a plate with a thickness set at $\lambda/4$ of a frequency between the resonant frequency $f_r$ and the antiresonant frequency $f_a$ of the piezoelectric transducer ($\lambda$ is the wavelength corresponding to the above-described frequency) is attached, and a solid resin layer obtained by applying and solidifying a liquid resin is formed on the radiation plane side. According to Japanese Patent Application Laid-Open No. 03-172096, it is said that, by making the acoustic matching layer a multilayer structure and polishing the above-described solid resin layer so as to compensate the bandwidth characteristics caused by the above-described plate, which is the first layer, the bandwidth characteristics can be made good and the productivity of the ultrasound probe can also be made good.

Furthermore, it is known that the acoustic impedance of acoustic matching layers and backing materials can be adjusted by mixing particles with resin materials such as epoxy resins.

For example, Japanese Patent Application Laid-Open No. 2005-177479 discloses an ultrasound transducer apparatus having an acoustic attenuation material containing 25 to 45 wt % of tungsten particles, 15 to 35 wt % of silicone particles, and 40 to 60 wt % of epoxy. In Japanese Patent Application Laid-Open No. 2005-177479, it is said that, when the acoustic attenuation material contains tungsten particles and silicone particles, the acoustic impedance can be decreased while maintaining the degree of acoustic attenuation.

Also, Japanese Patent Application Laid-Open No. 2012-235524 discloses a matching layer comprising a composite material comprising a matrix material loaded with a plurality of first heavy particles and a plurality of second light particles, wherein the plurality of second light particles has a density between about 100% to 200% of the desired composite density of the plurality of first heavy particles and the matrix material. In Japanese Patent Application Laid-Open No. 2012-235524, it is said that, when the matching layer contains the heavy particles and the light particles and the content of the heavy particles is adjusted, the acoustic impedance can be controlled. Also, in Japanese Patent Application Laid-Open No. 2012-235524, an epoxy resin is used as the matrix material, which is cured at room temperature. In addition, in Japanese Patent Application Laid-Open No. 2012-235524, it is said that tungsten particles, lead zirconate titanate (PZT) particles, gold particles, and platinum particles are used as the heavy particles, and silicon carbide particles and alumina particles are used as the light particles.

However, the tungsten particles as described in Japanese Patent Application Laid-Open Nos. 2005-177479 and 2012-235524 have a higher density than the resin material. Therefore, when the resin material is heated for curing, the viscosity of the resin is decreased before it is thermally cured, which may cause the particles to sediment easily. When the particles sediment, they may not be uniformly dispersed in the matching layer, resulting in a variation in acoustic impedance between areas where there are more particles present and areas where there are fewer particles present. Also, since the tungsten particles are metal particles, the cutting processability of the cured product may be decreased.

In addition, although tungsten is a material with high electrical resistance as a metal, there is a risk of short-circuiting when attempting to improve the output of the ultrasound probe or to accommodate a higher operating voltage.

Moreover, attempting to cure the resin material at room temperature, as described in Japanese Patent Application Laid-Open No. 2012-235524, can suppress the decrease in viscosity of the resin, but it also lengthens the time until the resin is cured, resulting in a decrease in production efficiency. Then, since the plurality of first heavy particles and the plurality of second light particles each have a higher density than the matrix material (resin material), there is a risk of particle sedimentation in the matching layer.

SUMMARY

The present invention has been made in view of the above-described circumstances, and an object thereof is to provide a resin composition that enables obtainment of a cured product in which particles are uniformly dispersed and can also enhance the short-circuiting resistance, cutting processability, and production efficiency of the cured product, as well as an acoustic member, an ultrasound transducer, an ultrasound probe, and an ultrasound diagnostic apparatus that comprise the cured product of the above-described resin composition.

A resin composition according to one embodiment of the present invention to solve the above-described problem is a resin composition used for producing an acoustic member used for an ultrasound probe, the resin composition comprising: a thermosetting resin; and two or more types of particles dispersed in the thermosetting resin, the two or more types of particles comprising: heavy particles that have a higher density than the thermosetting resin and are particles other than metal particles; and light particles that have a lower density than the thermosetting resin, and the total content of the heavy particles and the light particles relative to the entire volume of a cured product of the resin composition being 10 vol % or more.

Also, an acoustic member according to one embodiment of the present invention to solve the above-described problem is an acoustic member used for an ultrasound transducer, the acoustic member comprising the cured product of the above-described resin composition.

Also, an ultrasound transducer according to one embodiment of the present invention to solve the above-described problem is an ultrasound transducer comprising the above-described acoustic member.

Also, an ultrasound probe according to one embodiment of the present invention to solve the above-described problem is an ultrasound probe comprising the above-described ultrasound transducer.

Also, an ultrasound diagnostic apparatus according to one embodiment of the present invention to solve the above-described problem is an ultrasound diagnostic apparatus comprising the above-described ultrasound probe.

According to the present invention, a resin composition that enables obtainment of a cured product in which particles are uniformly dispersed and can enhance the short-circuiting resistance, cutting processability, and production efficiency of the cured product, as well as an acoustic member, an ultrasound probe, and an ultrasound diagnostic apparatus that comprise the cured product of the above-described resin composition, is provided.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Figure 1:
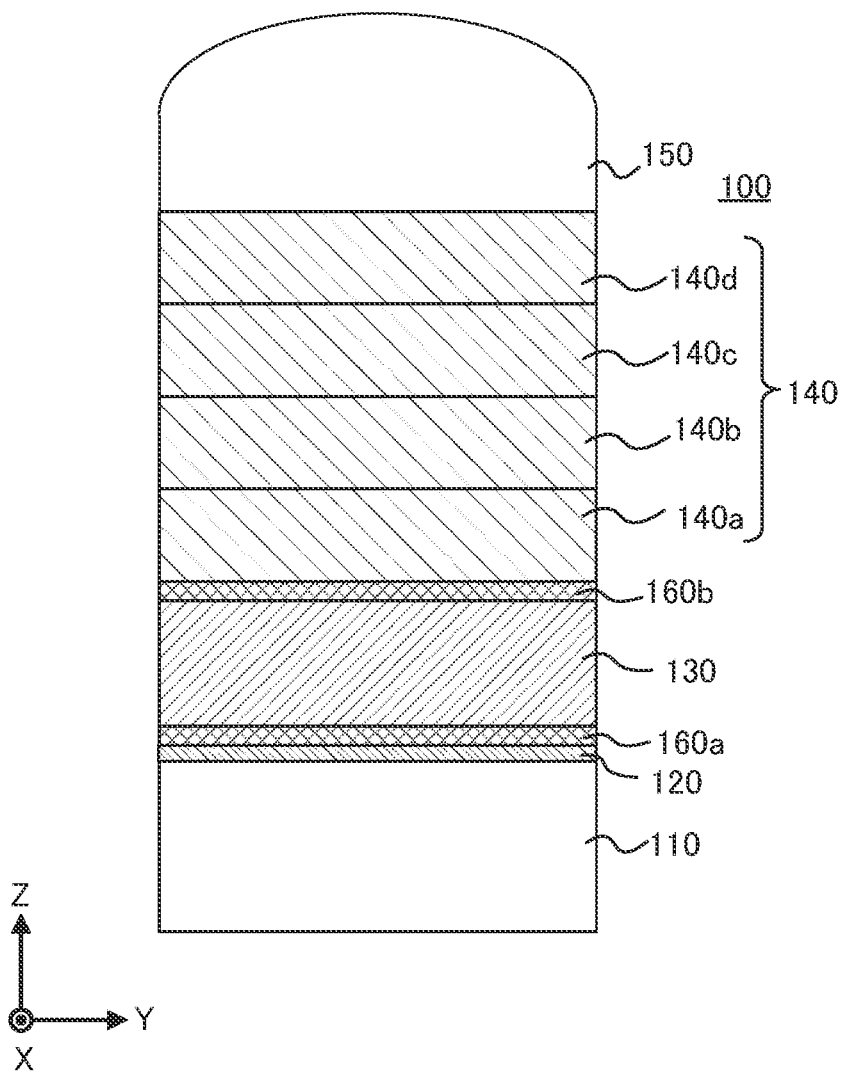
FIG. 1 is a cross-sectional view showing an example of the overall structure of an ultrasound transducer according to one embodiment of the present invention.

Hereinafter, one or more embodiments of the present invention will be described with reference to the drawings. However, the scope of the invention is not limited to the disclosed embodiments.

1. Resin Composition

The present invention relates to a resin composition used for an acoustic member included in an ultrasound transducer, which will be mentioned later. The resin composition according to one embodiment of the present invention comprises a thermosetting resin and two or more types of particles dispersed in the thermosetting resin.

1-1. Thermosetting Resin

The thermosetting resin is a resin that is cured by heating. Examples of the thermosetting resin include epoxy resins, urethane resins, and silicone resins. Among these, it is preferable that the thermosetting resin comprise an epoxy resin. When the thermosetting resin comprises an epoxy resin, it is possible to prevent warpage deformation or breakage of a cured product of the resin composition (hereinafter, simply referred to as the "cured product") due to shrinkage of the resin composition during curing, while enhancing the chemical resistance of the ultrasound probe during cleaning. Furthermore, when the thermosetting resin comprises an epoxy resin, the sound velocity and acoustic impedance in the cured product can be easily adjusted, and the propagation loss of ultrasound is less likely to occur when the cured product is used as an acoustic matching layer. In addition to these characteristics, when the thermosetting resin comprises an epoxy resin, expansion of the cured product due to temperature changes in the environment during production of the ultrasound transducer and expansion of the cured product due to heat generated by the piezoelectric material when using the ultrasound transducer can be suppressed. As a result of this, the piezoelectric material is less likely to be damaged due to the expansion of the cured product.

Examples of the epoxy resin include:

glycidyl ether epoxy resins, including bisphenol epoxy resins such as bisphenol A epoxy resins and bisphenol F epoxy resins;

glycidyl ester epoxy resins such as hydrophthalic acid epoxy resins and dimer acid epoxy resins;

glycidyl amine epoxy resins such as aromatic amine epoxy resins, aminophenol epoxy resins such as triglycidyl-p-aminophenol;

biphenyl novolac epoxy resins such as phenol novolac epoxy resins and cresol novolac epoxy resins; and phosphorus-modified epoxy resins, liquid crystalline epoxy resins, biphenyl aralkyl epoxy resins, biphenyl aralkyl epoxy resins, cyanuric acid epoxy resins, cyclic aliphatic epoxy resins, naphthalene skeleton epoxy resins, and long chain aliphatic epoxy resins.

Examples of commercially available products of the epoxy resin include jER828 (manufactured by Mitsubishi Chemical Corporation).

Among these, from the viewpoint of enhancing the storage stability of the resin composition, it is preferable that the epoxy resin be a glycidyl ether epoxy resin, a glycidyl ester epoxy resin, or a glycidyl amine epoxy resin.

Examples of the urethane resin for use include known polyurethane resins. Examples of the polyol compound that makes up the polyurethane resin include polyester polyols, polyether polyols, polycarbonate polyols, polyolefin polyols (including polyols formed by hydrogenating polydiene polyols), polybutadiene polyols, polyisoprene polyols, and acrylic resin polyols.

Examples of the silicone resin include room temperature-curable silicone rubbers, heating-curable silicone rubbers, condensation reaction type silicone rubber powders, and addition reaction type silicone rubbers. Specific examples thereof include methyl silicone resins, methyl phenyl silicone resins, organic resin-modified silicone resins, and silicone oligomers with alkoxy groups such as methoxy groups and ethoxy groups and reactive functional groups such as epoxy groups, methacryl groups, and mercapto groups.

The thermosetting resin may be a two-component type, in which a base resin and a curing agent are mixed at the time of curing, or it may be a one-component type.

The viscosity of the thermosetting resin (the base resin in the case of a two-component type) at 25° C. is not particularly limited, and is preferably 1 Pa·s or more and 30 Pa·s or less, more preferably 8 Pa·s or more and 20 Pa·s or less, and still more preferably 12 Pa·s or more and 15 Pa·s or less. If the viscosity is 1 Pa·s or more, both heavy particles and light particles, which will be mentioned later, are less likely to sediment when the resin composition is heated (at the time of curing), and if the viscosity is 30 Pa·s or less, the applicability of the resin composition of the present invention to the piezoelectric material of the ultrasound probe can be enhanced. Note that the term "applicability" as used herein refers to the ease of applying the resin composition to the base material, such as the piezoelectric material. Also, the above-described viscosity may be adjusted by mixing multiple thermosetting resins, may be adjusted by adding a reactive diluent such as an epoxy resin diluent, or may be adjusted by adding a solvent. However, from the viewpoint of suppressing agglomeration of the heavy particles or light particles or minimizing the time and labor required for drying after the application to enhance the production efficiency, it is preferable that the thermosetting resin not contain a reactive diluent or a solvent. The above-described viscosity can be measured by a rotational viscometer, an oscillational viscometer, or other means. In the present embodiment, the above-described viscosity is measured by a rheometer (manufactured by Anton Paar GmbH, MCR102).

The weight average molecular weight (Mw) of the thermosetting resin before curing is not particularly limited, and is preferably 150 or more and 50,000 or less, and more preferably 200 or more and 30,000 or less. When the above-described weight average molecular weight (Mw) is in the above-described range and is 150 or more, volatilization of the thermosetting resin before curing can be suppressed more and the durability of the cured product can be enhanced. Also, when the above-described weight average molecular weight (Mw) is 50,000 or less, the applicability of the resin composition can be enhanced more without increasing the viscosity of the thermosetting resin too much. The above-described weight average molecular weight (Mw) is measured by gel permeation chromatography (GPC) using polystyrene as the standard.

The density of the thermosetting resin before curing is not particularly limited as long as it is lower than that of the heavy particles and higher than that of the light particles, which will be mentioned later. From the viewpoint of facilitating adjustment of the acoustic impedance, the density of the thermosetting resin is preferably 1.0 g/cm³ or more and 1.4 g/cm³ or less, and more preferably 1.1 g/cm³ or more and 1.3 g/cm³ or less. With a density of the thermosetting resin of 1.0 g/cm³ or more, an acoustic impedance more sufficient to suppress reflection of the ultrasound in the ultrasound transducer can be obtained. With a density of the thermosetting resin of 1.4 g/cm³ or less, a decrease in acoustic impedance due to a decrease in sound velocity in the cured product of the resin composition can be suppressed more sufficiently. With a density of the thermosetting resin before curing of 1.1 g/cm³ or more and 1.3 g/cm³ or less, it is possible to cause hindered sedimentation in a larger number of particles among the particles contained in the thermosetting resin, which makes them more easily dispersed in the thermosetting resin.

In the present embodiment, the curing agent causes a crosslinking reaction with the thermosetting resin when heated at a temperature of 50° C. or higher and 200° C. or lower, thereby curing the thermosetting resin.

Examples of the curing agent used to cure epoxy resins among thermosetting resins include amine curing agents, imidazole curing agents, imidazolium salt curing agents, triazine trithiol curing agents, thiol curing agents, and acid anhydride curing agents.

Examples of the amine curing agent include chain aliphatic polyamines such as diethylenetriamine, triethylenetetramine, dipropylenediamine, diethylaminopropylamine, 2,2'-dimethyl-4,4'-methylenebis(cyclohexylamine), 4,4'-methylenebis(2-methylcyclohexanamine), and 3,3'-dimethyl-diaminodicyclohexylmethane; cyclic aliphatic polyamines such as N-aminoethylpiperazine, menthenediamine, and isophoronediamine; aromatic amines such as m-xylenediamine, metaphenylenediamine, diaminodiphenylmethane, and diaminodiphenylsulfone; and polyamide resins, piperidine, N,N-dimethylpiperazine, triethylenediamine, 2,4,6-tris(dimethylaminomethyl)phenol, benzyldimethylamine, 2-(dimethylaminomethyl)phenol, and trisdimethylaminomethylphenol.

Examples of the imidazole curing agent include imidazoles such as 2-methylimidazole, 2-ethylimidazole, 2-ethyl-4-methylimidazole, and 1-benzyl-2-methylimidazole.

Examples of the imidazolium salt curing agent include 1-cyanoethyl-2-undecylimidazolium trimellitate.

Examples of the thiol curing agent include:

hydrocarbon thiol curing agents such as 1,4-butanedithiol and 1,6-hexanedithiol;

ether thiol curing agents such as 3,6-dioxa-1,8-octanedithiol and 3,4-dimethoxybutane-1,2-dithiol; and alcoholic thiol curing agents such as 1,3-dimercapto-2-propanol and 2,3-dimercapto-1-propanol.

Examples of the acid anhydride curing agent include phthalic anhydride, trimellitic anhydride, methyltetrahydrophthalic anhydride, methyl endo-methylene-tetrahydrophthalic anhydride, methylbutenyltetrahydrophthalic anhydride, and methylhexahydrophthalic acid.

Among these, from the viewpoint of further enhancing heat resistance and chemical resistance, the curing agent is preferably an amine curing agent or an imidazole curing agent. Examples of commercially available products of the amine curing agent include jERCURE 113 (manufactured by Mitsubishi Chemical Corporation). Examples of the imidazole curing agent include CUREZOL 2E4MZ and CUREZOL 1B2MZ (both manufactured by Shikoku Chemicals Corporation).

As the curing agent used to cure urethane resins, isocyanate compounds can be used. Isocyanate compounds are compounds having two or more isocyanate groups in the molecule. Examples of the isocyanate compound include tolylene diisocyanate (TDI), diphenylmethane diisocyanate (MDI), naphthalene diisocyanate (NDI), tolidine diisocyanate (TODI), hexamethylene diisocyanate (HDI), isophorone diisocyanate (IPDI), phenylene diisocyanate, xylylene diisocyanate (XDI), tetramethylxylylene diisocyanate (TMXDI), cyclohexane diisocyanate, lysine ester diisocyanate, lysine ester triisocyanate (LDI), undecane triisocyanate, hexamethylene triisocyanate, triphenylmethane triisocyanate, and polymers, derivatives, modified forms, and hydrogenated forms of the above-described isocyanate compounds.

The content of the curing agent is not particularly limited. When commercially available products of the thermosetting resin are used, the amount specified for each product can be used.

The glass transition temperature $T_{g1}$ of the thermosetting resin after curing is not particularly limited, and is preferably 80° C. or higher and 200° C. or lower, and more preferably 100° C. or higher and 180° C. or lower. When the above-described $T_{g1}$ is 80° C. or higher, the glass transition temperature $T_{g1}$ of the resin composition can be increased, and therefore, the resin composition can be prevented from being cured when applying the resin composition. Furthermore, when the above-described $T_{g1}$ is 100° C. or higher, the chemical resistance of the cured product can be enhanced more. When the above-described $T_{g1}$ is 200° C. or lower, the time required for the resin composition to be cured can be shortened. Furthermore, when the above-described $T_{g1}$ is 180° C. or lower, the temperature difference until the temperature returns to ordinary temperature after curing is small, and therefore, it is possible to prevent warpage deformation caused by the difference in linear expansion coefficient between the resin composition and the substrate on which the resin composition is applied. The above-described glass transition temperature is measured using a differential scanning calorimeter "Diamond DSC" (manufactured by PerkinElmer, Inc.) under temperature rising and cooling conditions where the temperature rising and descending rate is 10° C./min and the temperature rising range is from 0° C. to 150° C.

1-2. Particles

The resin composition according to the present embodiment comprises two or more types of particles. The above-described two or more types of particles comprises heavy particles that have a higher density than the above-described thermosetting resin and light particles that have a lower density than the above-described thermosetting resin.

In the invention described in Japanese Patent Application Laid-Open No. 2012-235524, two or more types of particles are mixed in the resin, but since the densities of these particles are all higher than that of the resin, the above-described particles all tend to sediment when the viscosity of the thermosetting resin is decreased during heat curing, and sedimentation of the particles during heating occurs significantly. The occurrence of sedimentation results in unevenly distributed particles in the cured product. Therefore, when the above-described cured product is used as the acoustic member of the ultrasound probe, there is a risk of a variation in acoustic impedance between areas where there are more particles present and areas where there are fewer particles present.

Also, when only particles having a density lower than that of the resin are contained, the particles will float during heat curing, resulting in unevenly distributed particles in the resin. Therefore, as in the case where sedimentation occurs, there will be a variation in acoustic impedance in the matching layer.

In contrast, in the above-described resin composition, the particles that have a higher density than the resin and the particles that have a lower density than the resin are contained in the resin, causing hindered sedimentation to occur in the resin. As a result of this, sedimentation of the particles during heating can be suppressed and the dispersibility of the particles in the cured product can be enhanced.

Hindered sedimentation is a phenomenon in which particles sediment while being influenced by other particles that are sedimenting at the same time. When hindered sedimentation takes place, the sedimentation rate of particles becomes slower than when sedimentation takes place without the influence of other particles. In the resin composition of the present invention, the heavy particles try to sediment in the resin while the light particles try to float, causing them to interfere with each other and making it more difficult for the particles to sediment and float. Therefore, the resin can be cured before the particles sediment and float, causing a variation in the degree to which the particles are present, and the dispersibility of the particles in the cured product can be easily enhanced.

Also, when the thermosetting resin is cured at room temperature, as in the case of Japanese Patent Application Laid-Open No. 2012-235524, the viscosity of the thermosetting resin is less likely to be decreased compared to the case of curing by heating, and sedimentation of the particles can be suppressed. However, the time it takes for the thermosetting resin to be cured becomes longer than when it is cured by heating, which poses a problem of decreased production efficiency.

In contrast, in the above-described resin composition, since sedimentation of the particles during heating can be suppressed as mentioned above, curing by heating can be carried out while suppressing the sedimentation of the particles. The time required for curing can be shortened compared to curing at room temperature, thereby improving the production efficiency.

1-2-1. Heavy Particles

The heavy particles have a higher density than the thermosetting resin and are particles other than metal particles.

In the resin composition, only one type of heavy particles may be contained, or two or more types thereof may be contained. From the viewpoint of facilitating adjustment of the viscosity of the resin composition, it is preferable that two or more types be contained.

If metal particles such as tungsten particles are used as in Japanese Patent Application Laid-Open No. 2005-177479, when attempting to cut a cured resin composition, blade clogging, chipping, and deformation of the cured product may occur due to the malleability and ductility of the metal particles, resulting in decreased cutting processability. There is also a risk that the electrical conductivity of metal particles may decrease the short-circuiting resistance of the acoustic member. Although tungsten is a material with high electrical resistance as a metal, acoustic members used in ultrasound probes are required to have higher short-circuiting resistance than the conventional materials in order to improve the output of the ultrasound probe or to accommodate a higher operating voltage.

In addition, metals have a relatively large surface free energy and therefore have low affinity with resins, which have a relatively small surface free energy. Therefore, metal particles such as tungsten particles are believed to easily sediment in the resin composition. In contrast, inorganic materials other than metals have relatively low surface free energies, and therefore, particles of inorganic materials other than metals are considered less likely to sediment than metal particles.

Therefore, by using particles other than metal particles as the heavy particles, both cutting processability and short-circuiting resistance can be enhanced. Furthermore, the use of particles other than metals as the heavy particles can lower the surface energy of the particles and enhance their dispersibility in the thermosetting resin.

Examples of such a heavy particle material include ferrite, tungsten oxide, aluminum oxide, titanium oxide, tantalum oxide, niobium oxide, and zirconium oxide. Among these, from the viewpoint of further enhancing the dispersibility in the thermosetting resin, the heavy particle material is preferably a metal oxide, and from the viewpoint of further enhancing the cutting processability of the cured product of the resin composition, it is more preferably ferrite or tungsten oxide, and still more preferably ferrite.

From the viewpoint of further enhancing the short-circuiting resistance, it is preferable that the heavy particles be of an insulator or a semiconductor. Examples of the insulator include ferrite, aluminum oxide, titanium oxide, niobium oxide, and zirconium oxide. Examples of the semiconductor include tungsten oxide. Note that particles being "of an insulator or a semiconductor" as used herein means that the volume resistivity of such particles is $0.1 \ \Omega \cdot cm$ or more. Also, particles being "of an insulator" means that the volume resistivity of such particles is $10^6 \ \Omega \cdot cm$ or more.

The density of the heavy particles is not particularly limited as long as it is higher than that of the thermosetting resin, but it is preferably 2 times or more and 9 times or less compared to the density of the thermosetting resin, and more preferably 3 times or more and 7 times or less. If it is 2 times or more, the density of the resin composition can be increased more to make it easier to adjust to the desired acoustic impedance, and if it is 3 times or more, the density of the resin composition can be increased even more to make it much easier to adjust to the desired acoustic impedance. If it is 9 times or less, sedimentation of the heavy particles is less likely to occur, and if it is 7 times or less, sedimentation of the heavy particles is even less likely to occur.

From the viewpoint of making it easier to satisfy the above conditions, the heavy particles preferably have a density of 3.0 $g/cm^3$ or more and 10.0 $g/cm^3$ or less, preferably 3.5 $g/cm^3$ or more and 7.2 $g/cm^3$ or less, more preferably 4.0 $g/cm^3$ or more and 7.0 $g/cm^3$ or less, and still more preferably 4.0 $g/cm^3$ or more and 6.0 $g/cm^3$ or less. When the density is 3.5 $g/cm^3$ or more, it is possible to make hindered sedimentation with the light particles more likely to occur, and when the density is 7.2 $g/cm^3$ or less, the heavy particles are less likely to sediment.

The shape of the heavy particles is not particularly limited and may be spherical or irregularly shaped. From the viewpoint of making it difficult for the heavy particles to sediment, it is preferable that the heavy particles include irregularly shaped particles. Irregularly shaped particles have a larger surface area than spherical particles with the same mass, and particles tend to come into contact with each other. Therefore, when the heavy particles include irregularly shaped particles, hindered sedimentation is more likely to occur due to contact with the light particles. As a result of this, sedimentation of the particles is less likely to occur. Note that the term "irregularly shaped particles" as used herein refers to particles with irregularities on their surface, for example, particles with a sphericity of 0.9 or less. Whether the heavy particles are irregularly shaped or not can be determined by, for example, observing SEM images.

The particle diameter of the heavy particles is not particularly limited, and it is preferable that the heavy particles include particles having a particle diameter of 0.1 μm or more and 25.0 μm or less, it is more preferable that they include particles having a particle diameter of 0.5 μm or more and 22.5 μm or less, and it is more preferable that they include particles having a particle diameter of 0.8 μm or more and 20.0 μm or less. Since there is a positive correlation between the viscosity of the resin that contains particles and the specific surface area of the particles, when the heavy particles include particles having the above-described particle diameter of 0.1 μm or more, the total specific surface area of the heavy particles can be made small and the viscosity of the resin composition can be adjusted more easily, thus further enhancing the applicability of the resin composition. Also, when the heavy particles include particles having the above-described particle diameter of 25.0 μm or less, the cutting processability of the cured product of the resin composition can be further enhanced. Also, when the heavy particles include particles having a particle diameter described above in the above-described range, the acoustic impedance of the cured product can be easily adjusted. The above-described particle diameter and the particle size distribution are measured by cutting the cured product of the resin composition and processing the image taken of the cross section.

When the cured product of the resin composition is used as the acoustic matching layer, it is preferable that the particle diameter of the heavy particles be adjusted as appropriate in accordance with the center frequency of the ultrasound transducer. For example, when the thickness of the acoustic matching layer in the direction of propagation of ultrasound is set at ¼ of the wavelength, it is preferable that the particle diameter of the heavy particles be smaller than the above-described thickness. Specifically, when the sound velocity of ultrasound at a frequency of 10 MHz in the acoustic matching layer is 2,500 msec, the thickness of the acoustic matching layer in the direction of propagation of ultrasound is set at 62.5 μm. In this case, it is preferable that the particle diameter of the heavy particles contained in the resin composition (acoustic matching layer) be 62.5 μm or less. From the viewpoint of making it difficult for ultrasound to be attenuated, it is preferable for the heavy particles to have a particle diameter at which the cumulative value in the particle size distribution on a volume basis is 90% ($d_{90}$)), obtained by the above-described measurement method, of ⅛ or less of the wavelength of the ultrasound. As a result of this, it is possible to better suppress absorption or scattering of the ultrasound by the heavy particles, thus making it less likely that the ultrasound will be attenuated.

When the cured product of the resin composition is used as the backing material, it is preferable for the heavy particles to include particles having a particle diameter at which the cumulative value in the particle size distribution on a volume basis is 10% ($d_{10}$), obtained by the above-described measurement method, of ⅛ or more of the wavelength of the ultrasound. When the heavy particles include particles having a particle diameter ($d_{10}$) described above of ⅛ or more of the wavelength of the ultrasound, the heavy particles can easily absorb or scatter the ultrasound in the backing material, thus making it easier to attenuate the ultrasound.

It is preferable that the heavy particles include particles having a $d_{10}$ of 0.5 μm or more and a $d_{90}$ of 22.5 μm or less, the $d_{10}$ being a particle diameter at which the cumulative value in the particle size distribution on a volume basis is 10%, obtained by the above-described measurement method, the $d_{90}$ being a particle diameter at which the above-described cumulative value is 90%. When the heavy particles include particles having a $d_{10}$ of 0.5 μm or more, the applicability of the resin composition can be further enhanced, and when they include particles having a $d_{90}$ of 22.5 μm or less, the cutting processability of the cured product of the resin composition can be further enhanced. Also, when the heavy particles include particles having a particle size distribution as described above, the acoustic impedance of the cured product can be easily adjusted. From the above-described viewpoint, it is more preferable for the heavy particles to include particles having a $d_{10}$ of 0.8 μm or more and a $d_{90}$ of 20.0 μm or less, and it is still more preferable to include particles having a $d_{10}$ of 1.0 μm or more and a $d_{90}$ of 18.0 μm or less.

The particle diameter at which the cumulative value in the particle size distribution on a volume basis is 50% ($d_{50}$) of the heavy particles, obtained by the above-described measurement method, is not particularly limited, and it is preferable that the heavy particles include particles having a $d_{50}$ described above of 22.5 μm or less, it is preferable that they include particles having a $d_{50}$ of 0.5 μm or more and 22.5 μm or less, it is more preferable that they include particles having a $d_{50}$ of 0.8 μm or more and 20.0 μm or less, it is still more preferable that they include particles having a $d_{50}$ of 1.0 μm or more and 15.0 μm or less, and it is particularly preferable that they include particles having a $d_{50}$ of 1.0 μm or more and 14.0 μm or less. When the heavy particles include particles having a $d_{50}$ described above of 0.5 μm or more, the applicability of the resin composition can be further enhanced, and when they include particles having a $d_{50}$ of 22.5 μm or less, the cutting processability of the cured product of the resin composition can be further enhanced. Also, when the heavy particles include particles having a $d_{50}$ described above of in the above-described range, the acoustic impedance of the cured product can be easily adjusted. When the cured product of the resin composition is used as the acoustic matching layer, it is preferable that the heavy particles include particles having a $d_{50}$ of 22.5 μm or less from the viewpoint of making it difficult for the ultrasound to be attenuated.

The content of the heavy particles is not particularly limited, and is preferably 1 vol % or more and 30 vol % or less, more preferably 5 vol % or more and 20 vol % or less, and still more preferably 5 vol % or more and 15 vol % or less relative to the entire volume of the cured resin composition. When the above-described content is 1 vol % or more, it is possible to make hindered sedimentation with the light particles likely to occur, and when the content is 30 vol % or less, it is possible to make the heavy particles unlikely to sediment.

1-2-2. Light Particles

The light particles are particles that have a lower density than the thermosetting resin. Examples of such a light particle material include silicone rubbers and hollow glass beads. When the cured product of the resin composition is used as the backing material, it is preferable that the material of the light particles be an organic material from the viewpoint of making it easier for the ultrasound to be attenuated. Examples of the above-described organic material include silicone rubbers.

In the resin composition, only one type of light particles may be contained, or two or more types thereof may be contained. From the viewpoint of facilitating adjustment of the viscosity of the resin composition, it is preferable that two or more types be contained.

The density of the light particles is not particularly limited as long as it is lower than that of the thermosetting resin, but it is preferably 0.4 times or more and less than 1 time compared to the density of the thermosetting resin, and more preferably 0.8 times or more and less than 1 time. If it is 0.4 times or more, it becomes more difficult for the light particles to float in the resin composition, and if it is 0.8 times or more, it becomes even more difficult for the light particles to float in the resin composition. Also, when it is less than 1 time, the acoustic impedance can be easily adjusted to the desired one.

From the viewpoint of making it easier to satisfy the above conditions, it is preferable that the light particles include particles having a density of 0.5 $g/cm^3$ or more and 1.2 $g/cm^3$ or less, and it is more preferable that they include particles having a density of 0.8 $g/cm^3$ or more and 1.2 $g/cm^3$ or less. When the light particles include particles having a density of 0.5 $g/cm^3$ or more, it becomes more difficult for the light particles to float in the resin composition, and when they include particles having a density of 1.2 $g/cm^3$ or less, it is possible to make hindered sedimentation with the heavy particles more likely to occur.

The shape of the light particles is not particularly limited and may be spherical or irregularly shaped. From the viewpoint of increasing the surface area of the light particles and making it difficult for the light particles to sediment, it is preferable that the light particles include irregularly shaped particles. Irregularly shaped particles have a larger surface area than spherical particles with the same mass, and particles tend to come into contact with each other. Therefore, when the light particles include irregularly shaped particles, hindered sedimentation is more likely to occur due to contact with the heavy particles. As a result of this, sedimentation of the particles is less likely to occur. Whether the light particles are irregularly shaped or not can be determined by, for example, observing SEM images.

The particle diameter of the light particles is not particularly limited, and it is preferable that the light particles include particles having a particle diameter of 0.1 μm or more and 25.0 μm or less, it is more preferable that they include particles having a particle diameter of 0.5 μm or more and 22.5 μm or less, and it is still more preferable that they include particles having a particle diameter of 0.8 μm or more and 20.0 μm or less. When the light particles include particles having a particle diameter of 0.1 μm or more, the applicability of the resin composition can be further enhanced, and when they include particles having a particle diameter of 25.0 μm or less, the cutting processability of the cured product of the resin composition can be further enhanced. Also, when the light particles include particles having a particle diameter in the above-described range, the acoustic impedance can be easily adjusted. The above-described particle diameter is measured by cutting the cured product of the resin composition and processing the image taken of the cross section.

When the cured product of the resin composition is used as the acoustic matching layer, from the viewpoint of making it difficult for ultrasound to be attenuated, it is preferable for the light particles to have a particle diameter at which the cumulative value in the particle size distribution on a volume basis is 90% ($d_{90}$), obtained by the above-described measurement method, of ⅛ or less of the wavelength of the ultrasound. As a result of this, it is possible to better suppress absorption or scattering of the ultrasound by the light particles, thus making it less likely that the ultrasound will be attenuated.

When the cured product of the resin composition is used as the backing material, it is preferable for the light particles to include particles having a particle diameter at which the cumulative value in the particle size distribution on a volume basis is 10% ($d_{10}$), obtained by the above-described measurement method, of $\frac{1}{8}$ or more of the wavelength of the ultrasound. When the light particles include particles having a particle diameter ($d_{10}$) described above of $\frac{1}{8}$ or more of the wavelength of the ultrasound, the light particles can easily absorb or scatter the ultrasound in the backing material, thus making it easier to attenuate the ultrasound.

It is preferable that the light particles include particles having a $d_{10}$ of 0.5 μm or more and a $d_{90}$ of 22.5 μm or less, the $d_{10}$ being a particle diameter at which the cumulative value in the particle size distribution on a volume basis is 10%, obtained by the above-described measurement method, the $d_{90}$ being a particle diameter at which the above-described cumulative value is 90%. When the light particles include particles having a $d_{10}$ of 0.5 μm or more, the applicability of the resin composition can be further enhanced, and when they include particles having a $d_{90}$ of 22.5 μm or less, the cutting processability of the cured product of the resin composition can be further enhanced. Also, when the light particles include particles having a particle size distribution as described above, the acoustic impedance of the cured product can be easily adjusted. From the above-described viewpoint, it is more preferable for the light particles to include particles having a $d_{10}$ of 0.8 μm or more and a $d_{90}$ of 20.0 μm or less, and it is still more preferable to include particles having a $d_{10}$ of 1.0 μm or more and a $d_{90}$ of 18.0 μm or less.

The particle diameter at which the cumulative value in the particle size distribution on a volume basis is 50% ($d_{50}$) of the light particles, obtained by the above-described measurement method, is not particularly limited, and it is preferable that the light particles include particles having a $d_{50}$ described above of 22.5 μm or less, it is more preferable that they include particles having a $d_{50}$ of 0.5 μm or more and 22.5 μm or less, it is more preferable that they include particles having a $d_{50}$ of 0.8 μm or more and 20.0 μm or less, it is still more preferable that they include particles having a $d_{50}$ of 1.0 μm or more and 15.0 μm or less, and it is particularly preferable that they include particles having a $d_{50}$ of 1.0 μm or more and 14.0 μm or less. When the light particles include particles having a $d_{50}$ described above of 0.5 μm or more, the applicability of the resin composition can be further enhanced, and when they include particles having a $d_{50}$ of 22.5 μm or less, the cutting processability of the cured product of the resin composition can be further enhanced. Also, when the light particles include particles having a $d_{50}$ in the above-described range, the acoustic impedance can be easily adjusted.

It is preferable for the light particles to include particles having a smaller particle diameter at which the cumulative value in the particle size distribution on a volume basis is 50% ($d_{50}$) than that of the heavy particles, and it is more preferable that the above-described $d_{50}$ of the light particles be smaller than that of the heavy particles. Here, "the light particles include particles having a smaller $d_{50}$ than that of the heavy particles" means that, when the light particles include multiple types of particles of different materials, the $d_{50}$ of at least one of these particles is smaller than the $d_{50}$ of the entire heavy particles. Also, "the $d_{50}$ of the light particles is smaller than that of the heavy particles" means that the $d_{50}$ for the entire light particles is smaller than the $d_{50}$ for the entire heavy particles. When the cured product is used as the acoustic matching layer, even if the material of the light particles is an organic material that tends to attenuate ultrasound, light particles having a smaller $d_{50}$ than that of the heavy particles can make it less likely that the ultrasound will be attenuated.

Also, when the above-described $d_{50}$ of the light particles is smaller than the above-described $d_{50}$ of the heavy particles, sedimentation of the heavy particles can be suppressed more sufficiently. This is because there is a positive correlation between the specific surface area of particles and the viscosity of the solvent that contains the particles (thermosetting resin). Specifically, as the particle diameter of particles is smaller, the specific surface area of the particles is larger, which in turn increases the viscosity of the resin that contains the particles. Therefore, by making the above-described $d_{50}$ of the light particles smaller than that of the heavy particles, the viscosity of the thermosetting resin can be increased while allowing hindered sedimentation to occur. As a result of this, sedimentation of the heavy particles can be suppressed more sufficiently (see "Journal of the Society of Powder Technology, Japan, Vol. 27, No. 3 (1990), Rheological Behavior of Slurry to Dispersion State of Particles, Arakawa, M.").

Also, when the above-described $d_{50}$ of the light particles is smaller than the above-described $d_{50}$ of the heavy particles, formation of irregularities on the surface of the cured product of the resin composition can be suppressed and the appearance quality can be further enhanced. Although the reason for this is not clear, it is thought that, when the light particles are smaller than the heavy particles, the heavy particles can better suppress floating of the light particles, making it more difficult for the light particles to be oriented on the surface of the resin composition and suppressing the formation of irregularities.

The content of the light particles is not particularly limited, and is preferably 1 vol % or more and 30 vol % or less, more preferably 5 vol % or more and 20 vol % or less, and still more preferably 7 vol % or more and 20 vol % or less relative to the entire volume of the cured resin composition. When the above-described content is 1 vol % or more, it is possible to make hindered sedimentation with the heavy particles likely to occur, and when the content is 30 vol % or less, it is possible to make the light particles unlikely to float.

It is preferable that the content of the light particles be 0.3 times or more and 3 times or less compared to the content of the heavy particles. By adjusting the ratio between them, it is possible to make the heavy particles and the light particles more prone to hindered sedimentation and also to further enhance the dispersibility of the particles in the resin.

The total content of the heavy particles and the light particles relative to the entire volume of the cured product of the resin composition in the present embodiment is 10 vol % or more. When the total content is 10 vol % or more, the acoustic impedance of the cured product can be easily adjusted, and it is possible to cause sufficient hindered sedimentation of the heavy particles and the light particles to enhance their dispersibility. Also, a total content of 10 vol % or more can make the total specific surface area of the particles larger and increase the viscosity of the resin composition, thereby making it more difficult for the particles to sediment. The total content of the heavy particles and the light particles is preferably 10 vol % or more and 50 vol % or less, and more preferably 15 vol % or more and 35 vol % or less. When the total content of the heavy particles and the light particles is 50 vol % or less, an excessive increase in the viscosity of the resin composition can be suppressed and flowability can be ensured, making it easier for the resin composition to be applied to the piezoelectric material. Also, the above-described total content of the heavy particles and the light particles may be adjusted so that the acoustic impedance of the acoustic member will be in the range, which will be mentioned later. The above-described content may be calculated by cutting the cured product of the resin composition and processing the image taken to measure the amounts of the heavy particles and the light particles included in the cross section, or it may be calculated by carrying out compositional analysis using a SEM-EDX or the like.

In the present embodiment, by creating a calibration curve for the relationship between the content of the heavy particles and the light particles and the acoustic impedance of the cured product of the resin composition, it is possible to determine a content of the heavy particles and the light particles that will provide the desired acoustic impedance.

Note that the heavy particles and the light particles may be subjected to a surface treatment in order to further enhance their dispersibility. Examples of such a surface treatment method include subjecting the particles to a treatment with a solution containing a known silane coupling agent (primer), a plasma treatment, or other methods.

1-2-3. Physical Properties of Resin Composition

The glass transition temperature $T_{g2}$ of the cured product of the resin composition according to the present embodiment is not particularly limited, and is preferably 80° C. or higher. When the above-described $T_{g2}$ is 80° C. or higher, the resin composition can be prevented from being cured when applying the resin composition. Furthermore, when the above-described $T_{g2}$ is 100° C. or higher, the chemical resistance of the cured product can be enhanced more. When the above-described $T_{g2}$ is 200° C. or lower, the time required for the resin composition to be cured can be shortened. Furthermore, when the above-described $T_{g2}$ is 180° C. or lower, the temperature difference until the temperature returns to ordinary temperature after curing is small and the difference in linear expansion coefficient between the resin composition and the substrate on which the resin composition is applied can thus be made small, thereby making warpage deformation, which occurs when the cured product is cooled, less likely to occur. The glass transition temperature of the resin composition is measured in the same manner as the glass transition temperature of the thermosetting resin, as mentioned above.

The resin composition according to the present embodiment can be produced by mixing the above-described thermosetting resin, the above-described heavy particles, and the above-described light particles. The method for mixing them is not particularly limited, and from the viewpoint of making it difficult for the resin composition to contain air bubbles, it is preferable to carry out stirring in a vacuum. When carrying out the mixing, stirring may be performed while cooling from the viewpoint of suppressing a rapid temperature rise of the resin composition.

2. Acoustic Member

An acoustic member according to one embodiment of the present invention is an acoustic member used for an ultrasound probe, the acoustic member comprising the cured product of the above-described resin composition.

In the present embodiment, the acoustic member may be an acoustic matching layer of an ultrasound probe, a backing material, or those used for applications other than these.

The acoustic impedance of the acoustic member according to the present embodiment is preferably 1.7 MRayls or more and 15.0 MRayls or less, and more preferably 2.5 MRayls or more and 4.5 MRayls or less. When it is in the above-described range, the difference between the acoustic impedance of the acoustic member and the acoustic impedance of the acoustic lens of the ultrasound probe can be made small, making it difficult for the ultrasound to be reflected. In the present embodiment, since two or more types of particles, including the heavy particles and the light particles, are contained in the resin composition, the acoustic impedance of the acoustic member can be adjusted to the above-described range while suppressing sedimentation and floating of the particles.

The acoustic member according to the present embodiment may be produced by applying the above-described resin composition to a base material and curing it, or by molding it into a block form and curing it.

The viscosity of the above-described resin composition at the time of applying the above-described resin composition is preferably 1 Pa·s or more and 500 Pa·s or less, and more preferably 2 Pa·s or more and 150 Pa·s or less. When the above-described viscosity is 1 Pa·s or more, sedimentation of the particles can be better suppressed, and when the viscosity is 500 Pa·s or less, the applicability can be further improved. The above-described viscosity can be adjusted by adjusting the respective contents of the thermosetting resin, the heavy particles, and the light particles, as well as by controlling the temperature at which the resin composition is applied.

The method for applying the above-described resin composition is not particularly limited, and can be selected as appropriate from known methods. Examples of the method for applying the above-described resin composition include inkjet coating, die coating, bar coating, blade coating, and screen printing.

The temperature at the time of applying the above-described resin composition is not particularly limited and is set as appropriate in accordance with the method for application and the purpose. For example, when using the blade coating method, it is preferable to adjust the temperature of the coater to within ±5° C. of the temperature at which the viscosity of the resin composition is 1 Pa·s or more and 500 Pa·s or less to carry out the application, and it is more preferable to adjust the temperature of the coater to within ±5° C. of the temperature at which the viscosity of the resin composition is 2 Pa·s or more and 150 Pa·s or less to carry out the application. In this way, the thickness of the acoustic member in the direction of propagation of ultrasound can be adjusted to, for example, 10 μm or more and 500 μm or less.

Also, from the viewpoint of further improving the applicability, it is preferable that the above-described temperature be higher than ordinary temperature (25° C.) and lower than the curing temperature of the resin composition. When the above-described temperature is higher than ordinary temperature, the viscosity of the resin composition can be decreased to make it easier to apply the resin composition, and when the temperature is lower than the curing temperature, the resin composition can be prevented from being cured during the application.

The base material on which the above-described resin composition is applied is not particularly limited, and is, for example, a piezoelectric material.

Alternatively, from the viewpoint of carrying out maintenance such as cleaning in a simplified manner, it is preferably a base material from which the cured and produced acoustic member can be released. By using such a base material, for example, in cases where, on top of a matching layer to which microfabrication has been applied partially, another matching layer is pasted together, these matching layers can be detached from the substrate as a whole laminate, allowing for maintenance and replacement of the acoustic members in a simplified manner. Examples of such a base material include base materials including Teflon (Teflon is a registered trademark of The Chemours Company).

Note that the acoustic member according to the present embodiment may be applied on top of an acoustic member that contains a resin composition having a composition different from that of the above-described resin composition and that has a different function. As a result of this, a variety of acoustic members can be laminated without using adhesives, which can thus make attenuation of ultrasound due to adhesives less likely to occur.

Also, the above-described acoustic member may be molded into a block form. The method for molding it into a block form is carried out by following the procedures below, for example.

(1) A 100 mm square is die-cut from a 3 mm thick silicone rubber sheet, and the die-cut silicone rubber sheet is placed on a glass plate having a surface subjected to a water repellent treatment. (2) Next, the above-described resin composition is poured into the die-cut part of the silicone rubber sheet. (3) Another glass plate having a surface subjected to a water repellent treatment, prepared separately from the above-described glass plate, is placed on top of the silicone rubber sheet. (4) After heating the object made in (3) and curing the resin composition, the cured product is released from the silicone.

When the acoustic member is produced by applying the above-described resin composition, it is preferable that its thickness in the direction of propagation of ultrasound be 10 μm or more. When the above-described thickness is 10 μm or more, the acoustic impedance of the acoustic member can be easily adjusted to the above-described range. From the above-described viewpoint, the thickness of the acoustic member in the direction of propagation of ultrasound is preferably 10 μm or more and 500 μm or less, and more preferably 15 μm or more and 300 μm or less. When the above-described thickness is 500 μm or less, the applied resin composition is less likely to lose its shape due to the influence of gravity.

Alternatively, when the resin composition is molded into a block form to produce the acoustic member, it is preferable that the above-described thickness be 3,000 μm or less. When the above-described thickness is 3,000 μμm or less, the dispersibility of the particles in the resin composition during curing can be enhanced because heat can easily be uniformly conducted inside the resin during heat curing of the resin composition. Therefore, the acoustic impedance can be easily adjusted to the desired range. From the above-described viewpoint, the thickness of the acoustic member in the direction of propagation of ultrasound is preferably 100 μm or more and 3,000 μm or less. If the above-described thickness is 100 μm or more, when the cured product of the resin composition is released, it is possible to prevent the above-described cured product from being damaged

3. Ultrasound Transducer

3-1. Configuration of Ultrasound Transducer

An ultrasound transducer according to one embodiment of the present invention is an ultrasound transducer used for an ultrasound probe, comprising the above-described acoustic member.

FIG. 1 is a cross-sectional view showing an example of the overall structure of ultrasound transducer 100 according to one embodiment of the present invention.

As shown in FIG. 1, ultrasound transducer 100 has backing material 110, electrical terminal extraction section 120, piezoelectric material 130, acoustic matching layer 140, and acoustic lens 150. Hereinafter, each component will be described with reference to the accompanying drawings.

3-1-1. Backing Material

In the present embodiment, backing material 110 includes the above-described acoustic member. Also, backing material 110 is a member for supporting electrical terminal extraction section 120, piezoelectric material 130, and other components, which will be mentioned below, and functions as a member for attenuating the ultrasound that travels from piezoelectric material 130 to the rear side.

In the present embodiment, backing material 110 is constituted by a single layer, but backing material 110 may be constituted by multiple layers.

The thickness of backing material 110 in the direction of propagation of ultrasound is selected as appropriate in accordance with the material thereof, the wavelength of the ultrasound emitted by the ultrasound transducer, and other factors.

3-2. Electrical Terminal Extraction Section

Electrical terminal extraction section 120 is a member for transmitting signals to piezoelectric material 130 via signal electrodes 160a and 160b, and for receiving signals from piezoelectric material 130 via signal electrodes 160a and 160b. Such electrical terminal extraction section 120 is disposed between the above-described backing material 110 and piezoelectric material 130, which will be mentioned later. It is also electrically connected to an external power supply, a diagnostic apparatus, or the like.

3-3. Piezoelectric Material

Piezoelectric material 130 is disposed on electrical terminal extraction section 120 (in the present embodiment, on electrical terminal extraction section 120 via signal electrode 160a) and has a function of transmitting and receiving ultrasound.

The center frequency of the ultrasound emitted by piezoelectric material 130 is not particularly limited, and it is 1 MHz or more and 20 MHz or less, for example.

The thickness of piezoelectric material 130 in the direction of propagation of ultrasound is selected as appropriate in accordance with the type of ultrasound transducer and the frequency emitted by the ultrasound transducer, but it is 50 μm or more and 400 μm or less, for example.

Examples of the above-described piezoelectric material 130 include piezoelectric ceramics such as lead zirconate titanate (PZT); piezoelectric single crystals such as lead magnesium niobate-lead titanate solid solution (PMN-PT) and lead zinc niobate-lead titanate solid solution (PZN-PT); and composite piezoelectric materials in which these materials and polymeric materials are composited.

Also, multiple signal electrodes 160a and 160b, disposed on both surfaces of piezoelectric material 130, are electrodes for applying voltage to piezoelectric material 130. Signal electrodes 160a and 160b are not particularly restricted as long as they are electrically connected to the above-mentioned electrical terminal extraction section 120 and can also sufficiently transfer signals to and from piezoelectric material 130, and they can be layers made of gold, silver, copper, or the like, for example.

Note that, in the present embodiment, the ultrasound transducer has piezoelectric material 130 for transmitting and receiving ultrasound, but alternatively, it may have a piezoelectric material for transmitting ultrasound and a piezoelectric material for receiving ultrasound. These piezoelectric materials may be arranged in lamination or may be arranged in parallel. From the viewpoint of space saving, it is preferable that these piezoelectric materials be arranged in lamination.

3-4. Acoustic Matching Layer

In the present embodiment, acoustic matching layer 140 includes the above-described acoustic member. Acoustic matching layer 140 is a layer disposed on piezoelectric material 130 (in the present embodiment, on signal electrode 160*b* of piezoelectric material 130) to match the acoustic characteristics between piezoelectric material 130 and acoustic lens 150. Acoustic matching layer 140 may be constituted by a single layer, but it is normally constituted by multiple layers with different acoustic impedances. The number of layers in the acoustic matching layer is not particularly limited, and the acoustic matching layer is preferably constituted by two or more layers, and more preferably constituted by four or more layers. As shown in FIG. 1, in the present embodiment, acoustic matching layer 140 is a laminate that comprises first acoustic matching layer 140*a*, second acoustic matching layer 140*b*, third acoustic matching layer 140*c*, and fourth acoustic matching layer 140*d*.

The acoustic impedance of each layer constituting acoustic matching layer 140 can be adjusted by changing the type and amount of the thermosetting resin, the heavy particles, and the light particles in the above-described resin composition that constitutes each layer. Note that each acoustic matching layer 140*a*, 140*b*, or 140*c* may be a layer containing the same resin composition or a layer containing a different resin composition. Furthermore, the thickness of each layer may be the same or different.

The thickness of each acoustic matching layer in the direction of propagation of ultrasound is not particularly limited. From the viewpoint of easily adjusting the acoustic impedance to the desired range, it is known that the above-described thickness is preferably ¼ of the wavelength of ultrasound, but when the number of layers in the acoustic matching layer is two or more, the thickness of each layer is more preferably ⅛ or more and ¼ or less of the wavelength of ultrasound. As a result of this, the time from when the piezoelectric material stops vibration until it receives ultrasound (reverberation time) can be shortened, and it can also be made less likely that there will be a decrease in the sensitivity for the received ultrasound or a decrease in the signal strength. From the viewpoint of making it easier to satisfy the above conditions, the above-described thickness of each acoustic matching layer is preferably 10 μm or more and 500 μm or less, more preferably 15 μm or more and 500 μm or less, and still more preferably 15 μm or more and 250 μm or less.

3-5. Acoustic Lens

Acoustic lens 150 is a member for focusing the ultrasound transmitted from piezoelectric material 130. As shown in FIG. 1, in the present embodiment, acoustic lens 150 is a cylindrical acoustic lens extending in the Y direction and projecting in the Z direction of FIG. 1. The cross-sectional shapes perpendicular to the X direction are all identical. Also, such acoustic lens 150 focuses the ultrasound emitted by each piezoelectric material 130*a* in the z-direction and outputs it to the outside of ultrasound transducer 100.

Acoustic lens 150 is constituted by a material having acoustic characteristics suited for the object under inspection, for example, a living body. For example, it is preferable that acoustic lens 150 be constituted by a material having an acoustic impedance relatively close to that of the object under inspection, such as a silicone rubber.

3-2. Method for Producing Ultrasound Transducer

The method for producing the above-mentioned ultrasound transducer is not particularly limited as long as it is possible to provide the above-mentioned structure. One example of the method will be shown below, but it is not limited to the following.

A method for producing the ultrasound transducer in the present embodiment has: a step of forming backing material 110 on the rear side of piezoelectric material 130; a step of forming acoustic matching layer 140 on piezoelectric material 130; and a step of pasting acoustic matching layer 140 and acoustic lens 160 together.

3-2-1. Step of Forming Backing Material

In the present step, backing material 110 is formed on the surface of piezoelectric material 130 on the rear side with respect to the direction in which the ultrasound is transmitted.

In the present embodiment, the above-described resin composition is molded into a block form, which is then adhered to the rear side of piezoelectric material 130 to form backing material 110. The method for molding the above-described resin composition into a block form may be the same as the method described for the above-mentioned acoustic member. The method for applying the above-described resin composition is not particularly limited, and can be selected as appropriate from known methods. Examples of the method for applying the above-described resin composition include inkjet coating, die coating, bar coating, blade coating, and screen printing.

Note that backing material 110 may be formed on the rear side of piezoelectric material 130 by applying the above-described resin composition to a base material from which the formed backing material 110 can be released, and then adhering the above-described base material to piezoelectric material 130.

Backing material 110 may also be formed by applying the above-described resin composition to the rear side of piezoelectric material 130 and then curing the above-described resin composition.

The method for curing the above-described resin composition is not particularly limited. From the viewpoint of suppressing cure shrinkage of the resin composition, it is preferable to temporarily cure the resin composition at a temperature lower than its glass transition temperature and then heat cure it at a temperature higher than the glass transition temperature.

3-2-2. Step of Adhering Acoustic Matching Layer

In the present step, acoustic matching layer 140 is formed on the surface of piezoelectric material 130 in the direction of transmitting ultrasound.

In the present embodiment, the present step can be carried out by the following procedures.

(1) After applying the above-described resin composition on a substrate, the above-described resin composition is cured, (2) the cured resin composition is released from the substrate, (3) the cured product is cut to a size that allows it to be disposed on piezoelectric material 130, and (4) the cured product is then adhered to piezoelectric material 130.

In the above-described (1), when acoustic matching layer 140 is a laminate of multiple acoustic matching layers, a step of further applying an uncured resin composition on top of the above-described cured resin composition and then curing it is repeated. Also, the substrate to which the above-described resin composition is applied is not particularly limited as long as it is capable of releasing the cured product. The method for applying the above-described resin composition is the same as in the step of forming the backing material, and thus a detailed description will be omitted.

As described above, by the direct application and curing on the cured resin composition, the acoustic matching layer can be formed without using adhesive members such as adhesives between the layers of the acoustic matching layer. As a result of this, the propagation loss of ultrasound caused by the difference in acoustic impedance between the adhesive and the matching layer at the adhesive interface between the adhesive and the matching layer can be further reduced.

In the above-described (3), the method for cutting the cured product is not particularly limited, and it can be carried out by known methods.

In the above-described (4), the method for adhering the cured product to piezoelectric material 130 is not particularly limited, and the cured product can be adhered using known adhesives, for example.

Note that, in the present embodiment, the resin composition may be applied directly to piezoelectric material 130 and subsequently cured to form the acoustic matching layer.

Alternatively, the above-described resin composition may be molded into a block form, which is then adhered to the surface of piezoelectric material 130 in the direction of transmitting ultrasound.

3-2-3. Step of Pasting Acoustic Matching Layer and Acoustic Lens Together

In the present step, acoustic lens 160 is pasted on matching layer 140. The method for pasting the acoustic lens together is not particularly limited, and it may be adhered by known adhesives or by having adhesive layer 140 disposed in between.

4. Ultrasound Probe and Ultrasound Diagnostic Apparatus

Figure 2:
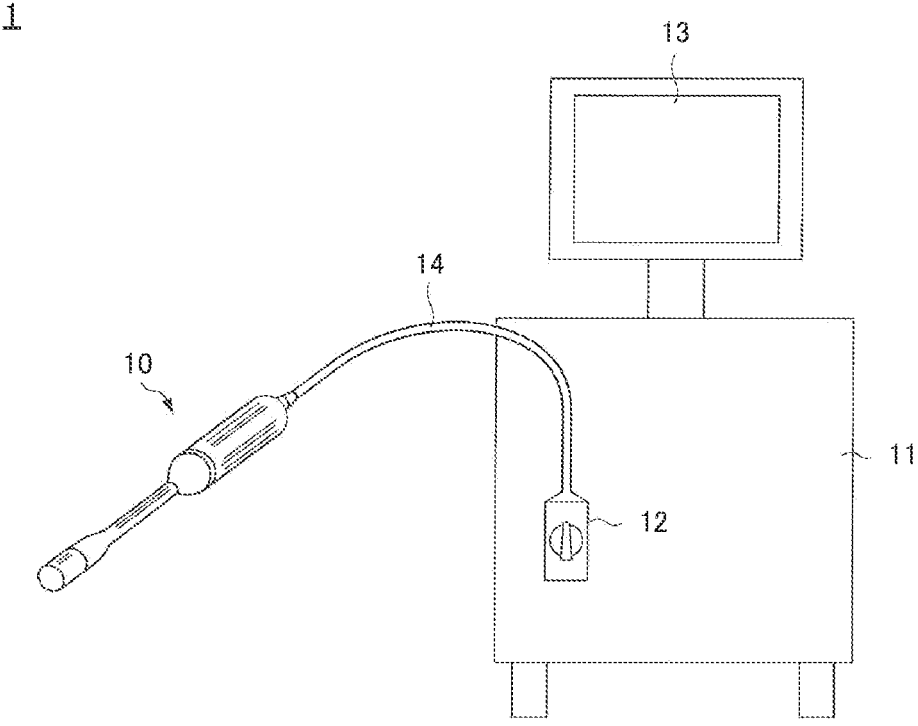
FIG. 2 shows the configuration of an ultrasound diagnostic apparatus.

The above-mentioned ultrasound transducer can be used for, for example, ultrasound probe 10, ultrasound diagnostic apparatus 1, and the like, as shown in FIG. 2. Ultrasound diagnostic apparatus 1 comprises ultrasound probe 10 equipped with the above-mentioned ultrasound transducer 100, main section 11, connector section 12, display 13, and other components.

Ultrasound probe 10 only needs to comprise the above-described ultrasound transducer (not shown) and is connected to main section 11 via cable 14 connected to connector section 12.

Electrical signals (transmitted signals) from main section 11 are transmitted through cable 14 to the piezoelectric material of ultrasound probe 10. These transmitted signals are converted into ultrasound by the piezoelectric material and then transmitted into the object under inspection. The transmitted ultrasound is reflected inside the object under inspection. Then, a portion of the reflected waves is received by the piezoelectric material, converted into electrical signals (received signals), and transmitted to main section 11. The received signals are converted into image data in main section 11 of ultrasound diagnostic apparatus 1 and displayed on display 13.

Ultrasound diagnostic apparatuses comprising the ultrasound transducer of the above-mentioned embodiment have high directivity and enable accurate diagnoses. Furthermore, the above-mentioned ultrasound transducer has high strength and can withstand shocks such as those caused by dropping, and thus can be used in ultrasound diagnostic apparatuses in a variety of fields.

EXAMPLES

1. Production of Acoustic Member

In the present Examples, the following items are used in the production of cured products of resin compositions (hereinafter, referred to as "acoustic members").

1-1. Thermosetting Resin 1-1-1. Base Resin epoxy resin base (Mitsubishi Chemical Corporation, jER828, density: 1.17 $g/cm^3$, viscosity: 12.0 Pa·s or more and 15.0 Pa·s or less)

1-1-2. Curing Agent epoxy resin curing agent 1 (Mitsubishi Chemical Corporation, jERCURE 113, curing start temperature of 152° C.)

epoxy resin curing agent 2 (Mitsubishi Chemical Corporation, ST12, curing temperature of 75° C.)

1-3. Heavy Particles ferrite powder 1 (Mn—Zn Ferrite particles, density: 4.9 $g/cm^3$)

ferrite powder 2 (JFE Chemical Corporation, KNI-106, density: 5.15 $g/cm^3$)

tungsten oxide powder (A.L.M.T. Corp., F1-WO3, density: 7.2 $g/cm^3$)

tungsten powder 1 (Japan New Metals Co., Ltd., W-5, density: 19.3 $g/cm^3$)

tungsten powder 2 (Japan New Metals Co., Ltd., W-2KD, density: 19.3 $g/cm^3$)

1-4. Light Particles silicone rubber powder (Shin-Etsu Chemical Co., Ltd., KMP-605, density: 0.99 $g/cm^3$)

For the above-described viscosity, the viscosity of the base resin was measured using a rheometer (manufactured by Anton Paar GmbH, MCR102).

The particle diameters of the heavy particles and the light particles were measured by using a laser diffraction/scattering particle size distribution analyzer. Based on the particle size distributions obtained from the measurements, the respective $d_{10}$, $d_{50}$, and $d_{90}$ of the heavy particles and the light particles were calculated.

Hereinafter, resin compositions were produced and applied in Experiments 1 to 15. Note that the "parts by volume" of the heavy particles and the light particles shown below refer to their volume relative to the volume of the cured resin composition. Note that Table 1 and Table 2 summarize the conditions of Experiments 1 to 15.

<Experiment 1>

The epoxy resin base, epoxy resin curing agent 1, ferrite powder 1 classified so that the particle diameter at which the cumulative value in the particle size distribution on a volume basis is 50% ($d_{50}$) was 5.5 μm or more and 6.4 μm or less, and the silicone rubber powder were introduced into a disposable cup and thoroughly mixed using a vacuum stirring apparatus (Thinky Corporation, ARV-310). At this time, the mixing was performed so that the contents of the heavy particles and the light particles relative to the entire volume of the cured product to be obtained after curing (hereinafter, referred to as the "volume filling rate") were 10.0% for ferrite powder 1 and 5.0% for the silicone rubber powder. At the time of mixing, stirring was performed while the disposable cup was being slowly cooled in order to suppress stirring heat caused by the rubbing of the contained particles against each other, thereby obtaining resin composition 1.

The above-described volume filling rate was calculated by cutting the cured product of the resin composition and processing the image taken to measure the amounts of the heavy particles and the light particles included in the cross section.

After the stirring, obtained resin composition 1 was applied to a glass substrate having a surface subjected to a water repellent treatment so that the thickness was 50 μm using an applicator (manufactured by Coating Tester Kogyo Corporation). Adjustment of the thickness was carried out by varying the width between the blade section of the applicator and the above-described glass substrate. At this time, the application was carried out while adjusting the temperature so that the viscosity of the resin composition was 14 Pa·s.

<Experiment 2>

Resin composition 2 was obtained and applied in the same manner as in Experiment 1 except that ferrite powder 1 was changed to ferrite powder 2.

<Experiment 3>

Resin composition 3 was applied in the same manner as in Experiment 1 except that the volume filling rate of ferrite powder 1 was changed to 12.5% and the volume filling rate of the silicone rubber powder was changed to 12.5%.

<Experiment 4>

Resin composition 4 was applied in the same manner as in Experiment 1 except that ferrite powder 1 was changed to the tungsten oxide powder.

<Experiment 5>

Resin composition 5 was applied in the same manner as in Experiment 1 except that the volume filling rate of ferrite powder 1 was changed to 1.5% and the volume filling rate of the silicone rubber powder was changed to 8.5%.

<Experiment 6>

Resin composition 6 was applied in the same manner as in Experiment 1 except that the volume filling rate of ferrite powder 1 was changed to 5.0% and the volume filling rate of the silicone rubber powder was changed to 10.0%.

<Experiment 7>

Resin composition 7 was applied in the same manner as in Experiment 1 except that the volume filling rate of ferrite powder 1 was changed to 11.5% and the volume filling rate of the silicone rubber powder was changed to 13.5%.

<Experiment 8>

Resin composition 8 was applied in the same manner as in Experiment 1 except that the volume filling rate of ferrite powder 1 was changed to 19.0% and the volume filling rate of the silicone rubber powder was changed to 16.0%.

<Experiment 9>

Resin composition 9 was applied in the same manner as in Experiment 6 except that it was applied so that the thickness of the acoustic member was 10 μm.

<Experiment 10>

A 100 mm square was die-cut from a 3 mm thick silicone rubber sheet, and the die-cut silicone rubber sheet was placed on a glass plate having a surface subjected to a water repellent treatment. Next, the resin composition obtained in Experiment 1 was poured into the die-cut part of the silicone rubber sheet. Then, another glass plate having a surface subjected to a water repellent treatment, prepared separately from the above-described glass plate, was placed on top of the silicone rubber sheet.

<Experiment 11>

Resin composition 11 was applied in the same manner as in Experiment 1 except that the volume filling rate of ferrite powder 1 was changed to 5.0% and the volume filling rate of the silicone rubber powder was changed to 1.0%.

<Experiment 12>

A thermosetting resin containing the epoxy resin base and epoxy resin curing agent 2, and ferrite powder 1 classified so that the particle diameter at which the cumulative value in the particle size distribution on a volume basis is 50% ($d_{50}$) was 5.5 μm or more and 6.4 μm or less were introduced into a disposable cup and thoroughly mixed using a vacuum stirring apparatus (Thinky Corporation, ARV-310). Ferrite powder 1 was mixed so that the volume filling rate was 3.0%. At the time of mixing, stirring was performed while the disposable cup was being slowly cooled in order to suppress stirring heat caused by the rubbing of the contained particles against each other, thereby obtaining resin composition 12.

After the stirring, obtained resin composition 11 was applied to a glass substrate having a surface subjected to a water repellent treatment so that the thickness was 50 μm using an applicator (manufactured by Coating Tester Kogyo Corporation), thereby applying the resin composition. At this time, the application was carried out while adjusting the temperature so that the viscosity of the resin composition was 14 Pa·s.

<Experiment 13>

A resin composition was applied in the same manner as in Experiment 12 except that a thermosetting resin containing the epoxy resin and epoxy resin curing agent 1 was used.

<Experiment 14>

Resin composition 14 was applied in the same manner as in Experiment 11 except that ferrite powder 1 was changed to tungsten powder 1 with a volume filling rate of 10.0% and 5.0 parts by volume of the silicone rubber was further added.

<Experiment 15>

Resin composition 15 was applied in the same manner as in Experiment 13 except that tungsten powder 1 was changed to tungsten powder 2.

1-5. Curing

Resin compositions 1 to 15, which had been applied or molded under the conditions of the above-described Experiments 1 to 15, were each placed in a thermostatic tank and temporarily cured in an environment at 40° C., 60° C., 80° C., and 100° C. The temporary curing time was set to 12 hours or longer in an environment at 40° C., 6 hours in an environment at 60° C., 4 hours in an environment at 80° C., and 2 hours in an environment at 100° C. Thereafter, the temporarily cured products obtained at the respective temporary curing temperatures were heat cured for 4 hours in an environment at 150° C. to produce acoustic members 1 to 15.

2. Evaluation

<Evaluation of Sedimentation>

The obtained acoustic members were observed in cross section for each temperature at which the temporary curing was carried out, and the presence or absence of sedimentation of the heavy and the light particles was evaluated based on the following criteria.

A No sedimentation of particles confirmed

C Sedimentation of particles confirmed, and unsuitable for use

<Production Speed>

For the production speed of the acoustic members, the time from the start of compounding the thermosetting resin, the heavy particles, and the light particles until the completion of heat curing at the highest curing temperature where the above-described sedimentation evaluation was A was defined as the "time taken to produce the acoustic member", which was evaluated based on the following criteria.

A The time taken until the final curing process was shorter than 8 hours

B The time taken until the final curing process was 8 hours or longer and shorter than 12 hours C The time taken until the final curing process was 12 hours or longer <Cuttability>

The acoustic members were cut 200 times with a dicing saw (DISCO Corporation, (DAD3350)) and a 25 μm wide dicing blade at 50 μm intervals with a cutting distance of 10 mm, and evaluated based on the following criteria.

A No deformation in the acoustic member during cutting

C Deformation occurs in the acoustic member during cutting, resulting in incorrect cutting <Short-Circuiting Resistance>

Ultrasound probes in which the acoustic members were incorporated as the acoustic matching layer were operated and their short-circuiting resistance was evaluated based on the following criteria.

A Operating properly with no problems

C Malfunction occurs due to a short circuit

<Acoustic Impedance>

The sound velocity c in the acoustic members was measured under conditions of 25° C. using a sing-around sound velocity measuring apparatus (manufactured by Ultrasonic Engineering Co., Ltd., UVM-2), by following the method described in JIS Z2353-2003. Next, the density p of the acoustic members was measured using a density measuring apparatus (AG245, manufactured by Mettler Toledo). Note that the above-described density measuring apparatus calculates the density $\rho$ of the acoustic members according to the expression (1) below. In the expression (1), A is the mass of the acoustic member in the atmosphere, B is the mass of the acoustic member in the displacement liquid, $\rho_0$ is the density of the displacement liquid, and $\rho_L$ is the density of the air. In the present Examples, pure water was used as the displacement liquid. Based on the obtained sound velocity c and density $\rho$, the acoustic impedance Z was calculated according to the expression (2) below.

$$\rho = (A/(A-B))(\rho_0 - \rho_L) + \rho_L \qquad (1)$$

$$Z = \rho c \qquad (2)$$

<Glass Transition Point>

Using a differential scanning calorimeter "Diamond DSC" (manufactured by PerkinElmer, Inc.), 3.0 mg of the sample was sealed in an aluminum pan and the temperature was varied in the order of heating, cooling, and heating. The temperature was raised from room temperature (25° C.) and from 0° C. for the first heating and for the second heating, respectively, to 200° C. at a temperature rising rate of 10° C./min, and held at 150° C. for 5 minutes. During cooling, the temperature was descended from 200° C. to 0° C. at a temperature descending rate of 10° C./min, and held at a temperature of 0° C. for 5 minutes. In the measurement curve obtained at the second heating, the shift of the baseline was observed, and the intersection of the extended line of the baseline before the shift and the tangent line showing the maximum slope of the shifted portion of the baseline was taken as the glass transition point (Tg). An empty aluminum pan was used as the reference.

<Comprehensive Evaluation>

Visual observation results on the appearance of the acoustic members and the comprehensive evaluation of the above-described sedimentation evaluation, production speed, cuttability, and short-circuiting resistance were evaluated based on the following criteria.

A No irregularities were confirmed on the surface of the acoustic member, and among the evaluations of sedimentation evaluation, production speed, cuttability, and short-circuiting resistance, C was one or less B Irregularities were confirmed on the surface of the acoustic member, but there were no problems in terms of quality, and among the evaluations of sedimentation evaluation, production speed, cuttability, and short-circuiting resistance, C was one or less C Irregularities were confirmed on the surface of the acoustic member to an unfavorable degree in terms of quality, or among the evaluations of sedimentation evaluation, production speed, cuttability, and short-circuiting resistance, C was two or more.

TABLE 1

| | No. | | | | | | | | | |
|---|---|---|---|---|---|---|---|---|---|---|
| | 1 | 2 | 3 | 4 | 5 | 6 | 7 | 8 | 9 | 10 |
| Type of heavy particles | Ferrite 1 | Ferrite 2 | Ferrite 1 | Tungsten oxide | Ferrite 1 | Ferrite 1 | Ferrite 1 | Ferrite 1 | Ferrite 1 | Ferrite 1 |
| $d_{10}$ of heavy particles [μm] | 1.7 | 0.6 | 1.7 | 0.5 | 1.7 | 1.7 | 1.7 | 1.7 | 1.7 | 1.7 |
| $d_{50}$ of heavy particles [μm] | 6.0 | 1.1 | 6.0 | 7.0 | 6.0 | 6.0 | 6.0 | 6.0 | 6.0 | 6.0 |
| $d_{90}$ of heavy particles [μm] | 22.5 | 1.2 | 22.5 | 15.0 | 22.5 | 22.5 | 22.5 | 22.5 | 22.5 | 22.5 |
| Filling rate of heavy particles [vol %] | 10.0 | 10.0 | 12.5 | 10.0 | 1.5 | 5.0 | 11.5 | 19.0 | 5.0 | 5.0 |
| Type of light particles | Silicone rubber | Silicone rubber | Silicone rubber | Silicone rubber | Silicone rubber | Silicone rubber | Silicone rubber | Silicone rubber | Silicone rubber | Silicone rubber |
| $d_{10}$ of light particles [μm] | 1.6 | 1.6 | 1.6 | 1.6 | 1.6 | 1.6 | 1.6 | 1.6 | 1.6 | 1.6 |
| $d_{50}$ of light particles [μm] | 2.2 | 2.2 | 2.2 | 2.2 | 2.2 | 2.2 | 2.2 | 2.2 | 2.2 | 2.2 |
| $d_{90}$ of light particles [μm] | 3.6 | 3.6 | 3.6 | 3.6 | 3.6 | 3.6 | 3.6 | 3.6 | 3.6 | 3.6 |
| Filling rate of light particles [vol %] | 5.0 | 5.0 | 12.5 | 5.0 | 8.5 | 10.0 | 13.5 | 16.0 | 10.0 | 13.5 |
| Total filling rate of particles [vol %] | 15.0 | 15.0 | 25.0 | 15.0 | 10.0 | 15.0 | 25.0 | 35.0 | 15.0 | 18.5 |
| Thickness [μm] | 50 | 50 | 50 | 50 | 50 | 50 | 50 | 50 | 10 | 3000 |
| Production method | Application | Application | Application | Application | Application | Application | Application | Application | Application | Molding |

TABLE 2

| | No. | | | | |
|---|---|---|---|---|---|
| | 11 | 12 | 13 | 14 | 15 |
| Type of heavy particles | Ferrite 1 | Ferrite 1 | Ferrite 1 | Tungsten 1 | Tungsten 2 |
| $d_{10}$ of heavy particles [μm] | 1.7 | 1.7 | 1.7 | 2.4 | 0.7 |
| $d_{50}$ of heavy particles [μm] | 6.0 | 6.0 | 6.0 | 5.3 | 1.5 |
| $d_{90}$ of heavy particles [μm] | 22.5 | 22.5 | 22.5 | 9.5 | 2.4 |
| Filling rate of heavy particles [vol %] | 5.0 | 3.0 | 3.0 | 10.0 | 10.0 |
| Type of light particles | Silicone rubber | None | None | Silicone rubber | Silicone rubber |
| $d_{10}$ of light particles [μm] | 1 | — | — | 1.6 | 1.6 |
| $d_{50}$ of light particles [μm] | | — | — | 2.2 | 2.2 |
| $d_{90}$ of light particles [μm] | 4 | — | — | 3.6 | 3.6 |
| Filling rate of light particles [vol %] | 1.0 | — | — | 5.0 | 5.0 |
| Total filling rate of particles [vol %] | 6.0 | 3.0 | 3.0 | 15.0 | 15.0 |
| Thickness [μm] | 50 | 50 | 50 | 50 | 50 |
| Production method | Application | Application | Application | Application | Application |

TABLE 3

| | | No. | | | | | | | | | |
|---|---|---|---|---|---|---|---|---|---|---|---|
| | | 1 | 2 | 3 | 4 | 5 | 6 | 7 | 8 | 9 | 10 |
| Sedimentation | Temporary curing temperature: 40 degrees | A | A | A | A | A | A | A | A | A | A |
| | Temporary curing temperature: 60 degrees | A | A | A | A | A | A | A | A | A | A |
| | Temporary curing temperature: 80 degrees | A | A | A | A | A | A | A | A | A | A |
| | Temporary curing temperature: 100 degrees | A | A | A | A | A | A | A | A | A | A |
| | Cuttability | A | A | A | A | A | A | A | A | A | A |
| | Short-circuiting resistance | A | A | A | A | A | A | A | A | A | A |
| | Production speed | A | A | A | A | A | A | A | A | A | — |
| | Comprehensive evaluation | A | B | A | A | A | A | A | A | A | A |
| | Acoustic impedance | Unmeasured | Unmeasured | 3.1 | Unmeasured | 3.6 | 3.6 | 3.6 | 3.6 | 3.6 | 3.6 |
| | Glass transition point $T_g$ [° C.] | 149 | 149 | 149 | 149 | 149 | 149 | 149 | 149 | 149 | 149 |

TABLE 4

| | No. | | | | |
|---|---|---|---|---|---|
| | 11 | 12 | 13 | 14 | 15 |
| Temporary curing temperature: 40 degrees | A | A | A | C | A |
| Temporary curing temperature: 60 degrees | A | A | C | C | A |
| Temporary curing temperature: 80 degrees | C | C | C | C | A |
| Temporary curing temperature: 100 degrees | C | C | C | C | A |
| Cuttability | A | A | A | C | C |
| Short-circuiting resistance | A | A | A | C | C |
| Production speed | C | C | C | Unmeasured | A |
| Comprehensive evaluation | C | C | C | C | C |
| Acoustic impedance | 3.3 | 3.3 | 3.3 | 3.6 | 3.6 |
| Glass transition point $T_g$ [° C.] | 149 | 76 | 149 | 149 | 149 |

Acoustic members 1 to 10 exhibited better results than acoustic members 11 to 14, with no sedimentation of the particles confirmed at each of the temporary curing temperatures. This is thought to be because hindered sedimentation occurred in the resin compositions containing the heavy particles and the light particles, making it difficult for the particles to sediment. Also, in Experiments 1 and 3 to 10, the comprehensive evaluation, including the appearance of the acoustic members, was more favorable. This is thought to be because the $d_{50}$ of the light particles was smaller than the $d_{50}$ of the heavy particles, which could thus improve the appearance quality of the acoustic members.

In contrast, poor results of acoustic member 11 are thought to be because the total volume filling rate of the heavy particles and the light particles was less than 10%, making it difficult for the heavy particles and the light particles to undergo hindered sedimentation. In acoustic members 12 and 13, since the resin compositions that contained only heavy particles and no light particles were used, it is thought that hindered sedimentation did not occur and the particles sedimented. In particular, the curing agent contained in acoustic member 13 has a high curing temperature and takes a long time to be cured, which is thought to have facilitated sedimentation before curing. Also, in acoustic member 14, the specific surface area of the tungsten particles contained in the resin composition was smaller than that in acoustic member 15, thus decreasing the viscosity of the resin composition, which is thought to have caused more sedimentation than in acoustic member 15.

In addition, acoustic members 1 to 10 exhibited better results than acoustic members 14 and 15 in terms of cuttability and short-circuiting resistance, as well. This is thought to be because the heavy particles were particles other than metal particles, which could make them less likely to cause blade chipping and less likely to conduct electricity.

The resin composition according to the present invention enables obtainment of a cured product in which particles are uniformly dispersed and can enhance the short-circuiting resistance, cutting processability, and production efficiency of the cured product. Therefore, the acoustic member formed by curing the above-described resin composition is useful in the field of ultrasound diagnoses, for example.

Although embodiments of the present invention have been described and illustrated in detail, the disclosed embodiments are made for purpose of illustration and example only and not limitation. The scope of the present invention should be interpreted by terms of the appended claims

What is claimed is:

1. An ultrasound transducer used for an ultrasound probe, comprising a backing material and an acoustic matching layer, the acoustic matching layer comprising a cured product of a resin composition, the resin composition comprising:
a thermosetting resin; and
two or more types of particles dispersed in the thermosetting resin,
the two or more types of particles comprising:
heavy particles that have a higher density than the thermosetting resin and are particles other than metal particles; and
light particles that have a lower density than the thermosetting resin, and a total content of the heavy particles and the light particles relative to an entire volume of the cured product of the resin composition being 10 vol % or more,
wherein the thermosetting resin consists of an epoxy resin or a urethane resin.

2. The ultrasound transducer according to claim 1, wherein the light particles have a smaller particle diameter at which a cumulative value in a particle size distribution on a volume basis is 50% ($d_{50}$) than the heavy particles.

3. The ultrasound transducer according to claim 1, wherein the heavy particles are particles having a density of 3.5 g/cm$^3$ or more and 7.2 g/cm$^3$ or less.

4. The ultrasound transducer according to claim 1, wherein the heavy particles are particles made of an insulator or a semiconductor.

5. The ultrasound transducer according to claim 1, wherein the cured product has a glass transition temperature of 80° C. or higher.

6. The ultrasound transducer according to claim 1, wherein the heavy particles comprise particles having a $d_{10}$ of 0.5 μm or more and a $d_{90}$ of 22.5 μm or less, the $d_{10}$ being a particle diameter at which a cumulative value in a particle size distribution on a volume basis is 10%, the $d_{90}$ being a particle diameter at which the cumulative value is 90%.

7. The ultrasound transducer according to claim 1, wherein the light particles comprise particles having a $d_{10}$ of 0.5 μm or more and a $d_{90}$ of 22.5 μm or less, the $d_{10}$ being a particle diameter at which a cumulative value in a particle size distribution on a volume basis is 10%, the $d_{90}$ being a particle diameter at which the cumulative value is 90%.

8. The ultrasound transducer according to claim 1, wherein the cured product has a thickness in a direction of propagation of ultrasound of 10 μm or more.

9. The ultrasound transducer according to claim 1, wherein the cured product has a thickness in a direction of propagation of ultrasound of 3,000 μm or less.

10. An ultrasound probe comprising the ultrasound transducer according to claim 1.

11. An ultrasound diagnostic apparatus comprising the ultrasound probe according to claim 10.

* * * * *